(12) United States Patent
Mou et al.

(10) Patent No.: US 10,935,529 B2
(45) Date of Patent: Mar. 2, 2021

(54) PORTABLE DEVICE INCLUDING A GAS DETECTING MODULE FOR MONITORING ENVIRONMENTAL AIR CONDITIONS

(71) Applicant: Microjet Technology Co., Ltd., Hsinchu (TW)

(72) Inventors: Hao-Jan Mou, Hsinchu (TW); Shih-Chang Chen, Hsinchu (TW); Chi-Chang Yang, Hsinchu (TW); Chiu-Lin Lee, Hsinchu (TW); Jia-Yu Liao, Hsinchu (TW); Ching-Sung Lin, Hsinchu (TW); Chih-Kai Chen, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 152 days.

(21) Appl. No.: 16/265,582

(22) Filed: Feb. 1, 2019

(65) Prior Publication Data

US 2019/0302072 A1    Oct. 3, 2019

(30) Foreign Application Priority Data

Mar. 30, 2018    (TW) .............................. 107111397 A

(51) Int. Cl.
*G01N 33/00*    (2006.01)
*G01N 1/22*    (2006.01)

(52) U.S. Cl.
CPC ....... *G01N 33/0009* (2013.01); *G01N 1/2273* (2013.01); *G01N 33/004* (2013.01); *G01N 33/0047* (2013.01); *G01N 2001/2276* (2013.01)

(58) Field of Classification Search
None
See application file for complete search history.

(56) References Cited

U.S. PATENT DOCUMENTS 6,165,347 A * 12/2000 Warburton ......... G01N 27/4045
204/409
2008/0262321 A1* 10/2008 Erad .................... G01N 21/253
600/301

(Continued)

FOREIGN PATENT DOCUMENTS

EP    2905673 A2    8/2015
EP    3203075 A1    8/2017

(Continued)

OTHER PUBLICATIONS

Extended European Search Report, dated Oct. 15, 2019, for European Application No. 19154837.9.

*Primary Examiner* — Harshad R Patel
*Assistant Examiner* — Nigel H Plumb
(74) *Attorney, Agent, or Firm* — Birch, Stewart, Kolasch & Birch, LLP

(57) ABSTRACT

A gas detecting module includes a carrying plate, a sensor, a compartment body and an actuator. The carrying plate has a substrate and a gas opening. The compartment body is divided into a first compartment and a second compartment by a partition plate. The first compartment has an opening. The second compartment has an outlet and accommodates the actuator. The bottom of the compartment body has an accommodation recess receiving the carrying plate, whereby the gas opening is aligned with the outlet, and the sensor packaged on the substrate is disposed within the first compartment through the opening. The partition plate has a notch. The gas detecting module is assembled in a slim-type portable device having a casing. The casing has an inlet aligned with the first compartment. As the actuator is actu- (Continued)

ated, ambient gas is inhaled into the first compartment, and the sensor detects the gas flowing therethrough.

13 Claims, 13 Drawing Sheets

(56) References Cited

U.S. PATENT DOCUMENTS

| | | | | |
|---|---|---|---|---|
| 2015/0219608 A1* | 8/2015 | Choi | ................ | G06F 1/1694 |
| | | | | 73/23.2 |
| 2016/0363339 A1* | 12/2016 | Blackley | ................ | H04L 67/125 |
| 2017/0218936 A1* | 8/2017 | Chen | ................ | F16K 99/0015 |
| 2018/0066645 A1* | 3/2018 | Mazur | ................ | A24F 47/002 |

FOREIGN PATENT DOCUMENTS

| | | |
|---|---|---|
| TW | 201616116 A | 5/2016 |
| TW | M538545 U | 3/2017 |
| TW | M544653 U | 7/2017 |
| TW | M551655 U | 11/2017 |
| TW | M552227 U | 11/2017 |
| TW | M552540 U | 12/2017 |
| WO | WO 2008/024138 A1 | 2/2008 |
| WO | WO 2012/154029 A1 | 11/2012 |
| WO | WO 2018/006932 A1 | 1/2018 |

* cited by examiner

PORTABLE DEVICE INCLUDING A GAS DETECTING MODULE FOR MONITORING ENVIRONMENTAL AIR CONDITIONS

FIELD OF THE INVENTION

The present disclosure relates to a slim-type portable device, and more particularly to a slim-type portable device housing a gas detecting module for monitoring ambient gas.

BACKGROUND OF THE INVENTION

Nowadays, people pay much attention to the air quality in the environment. For example, it is important to monitor carbon monoxide, carbon dioxide, volatile organic compounds (VOC), Particulate Matter (PM2.5), nitric oxide, sulfur monoxide, and so on. The exposures of these substances in the environment will cause human health problems or even threaten the human life. Therefore, it is important for every country to monitor the air quality in the environment.

Generally, it is feasible to use a gas sensor to monitor the air quality in the environment. If the gas sensor is capable of immediately providing people with the monitored information relating to the environment for caution, it may help people escape or prevent from the injuries and influence on human health caused by the exposure of the substances described above in the environment. In other words, the gas sensor is suitably used for monitoring the ambient air in the environment.

Generally, portable devices are the mobile devices that are usually carried by the people when they go out. Therefore, people pay much attention to the portable device having a gas detecting module embedded therein. More particularly, the developing trend of the current portable device is light and slim and must have high performance. Therefore, it is important to reduce the thickness of the gas detecting module, assemble the gas detecting module in the portable device and prevent the processor or other components within the portable device from interfering the gas detection.

SUMMARY OF THE INVENTION

An object of the present disclosure is to provide a slim-type portable device. A gas detecting module is suitable to be assembled in the slim-type portable device for monitoring ambient gas.

In accordance with an aspect of the present disclosure, a slim-type portable device is provided. The slim-type portable device includes a gas detecting module and a casing. The gas detecting module includes a carrying plate, a sensor, a compartment body and an actuator. The carrying plate has a substrate provided with a gas opening. A sensor is packaged on and electrically connected to the substrate. The compartment body has a partition plate disposed therein to divide an interior of the compartment body into a first compartment and a second compartment. The first compartment has an opening. The second compartment has an outlet. The bottom of the compartment body has an accommodation recess for allowing the carrying plate to be partially received and positioned therein so that the bottom of the compartment body is covered by the carrying plate. The gas opening of the substrate is aligned with the outlet of the second compartment, and the sensor disposed on the substrate penetrates the opening of the first compartment and is disposed within the first compartment. The partition plate has a notch for allowing the first compartment and the second compartment to be in fluid communication with each other. The actuator is disposed within the second compartment and separated from the sensor disposed within the first compartment so that the heat generated from the actuator is blocked from affecting the detection result of the sensor. The actuator covers the bottom of the second compartment and is actuated to generate a flow of gas that flows out of the outlet of the second compartment, and then is discharged into an environment outside the compartment body via the gas opening of the substrate. The gas detecting module is assembled in the casing. The casing covers the gas detecting module and has an inlet aligned with the first compartment of the compartment body. As the actuator is actuated, the gas around the slim-type portable device is inhaled into the first compartment through the inlet, and the sensor measures the gas flowing through the surface of the sensor. The gas is transported to the second compartment through the notch of the partition plate and then is discharged into the environment outside the compartment body via the outlet and the gas opening of the substrate. In this way, the gas flows in one way and is monitored.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

Figure 1A:
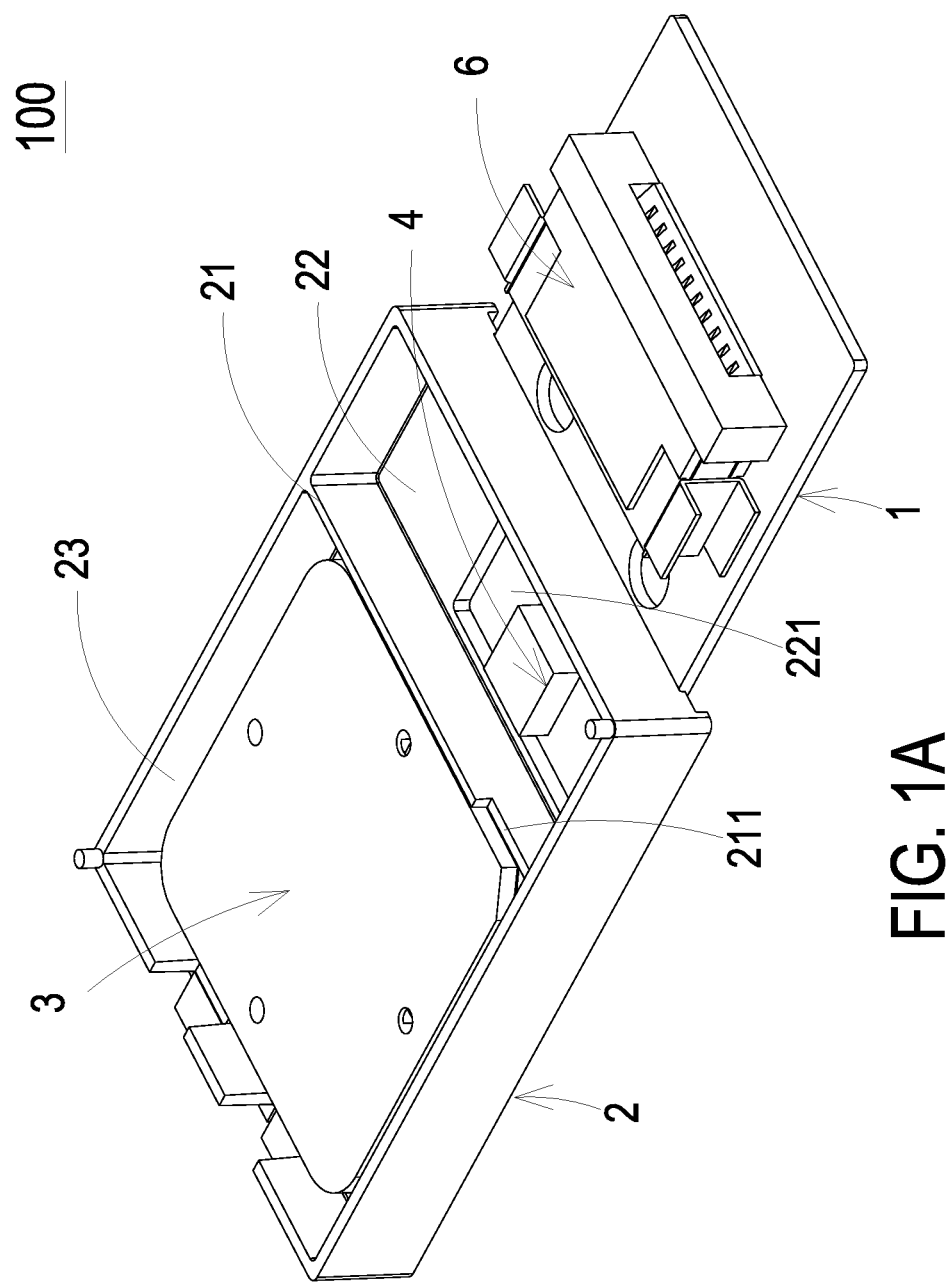
FIG. 1A is a schematic perspective view illustrating a gas detecting module according to an embodiment of the present disclosure.
Figure 1B:
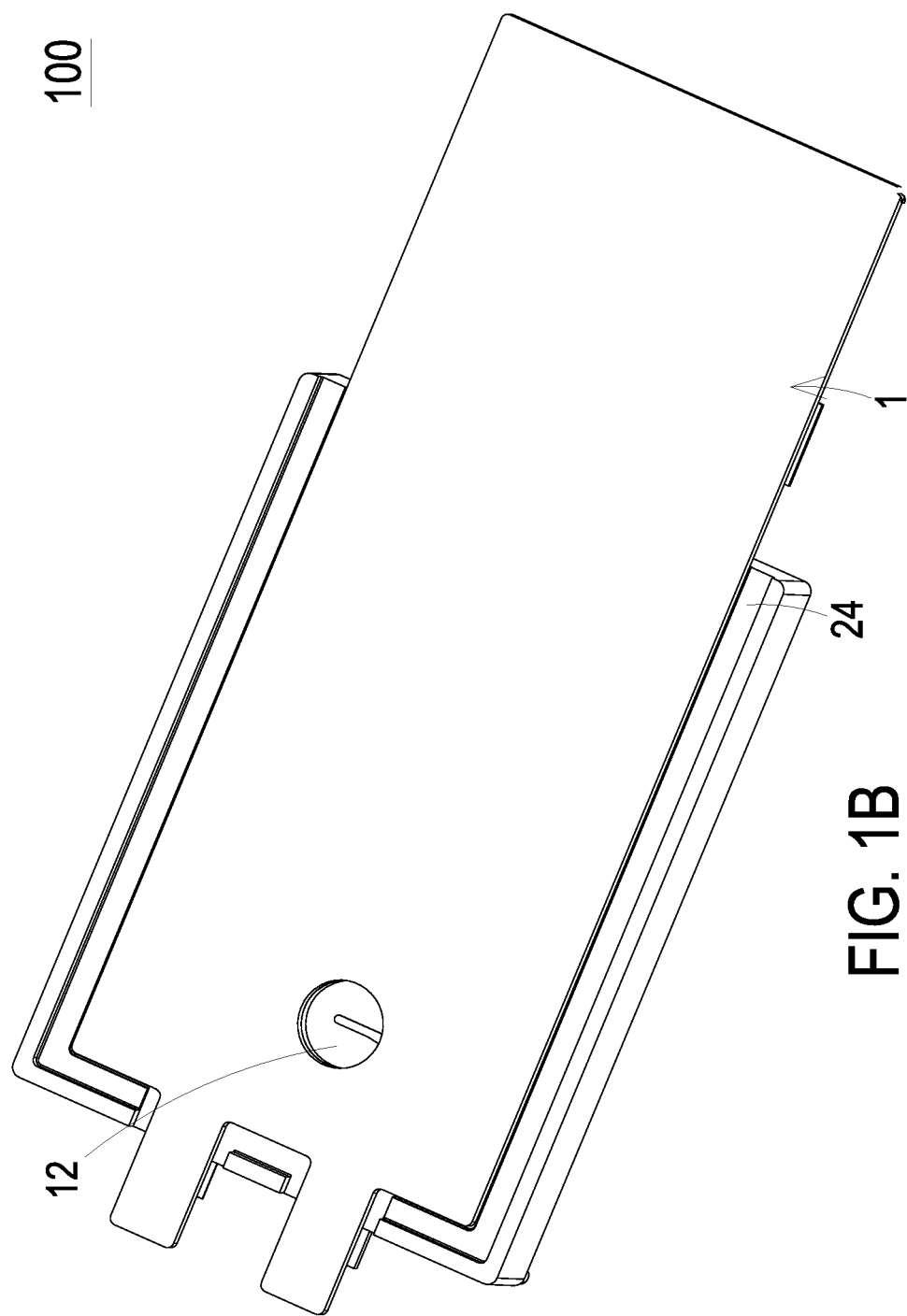
FIG. 1B is a schematic bottom view illustrating the gas detecting module of FIG. 1A.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIGS. 1A, 1B, 2, 3A, 3B and 3C. The present discourse provides a slim-type portable device 5 including at least one gas detecting module 100 including at least one carrying plate 1, at least one compartment body 2, at least one actuator 3, at least one sensor 4, at least one substrate 11, at least one gas opening 12, at least one partition plate 21, at least one first compartment 22, at least one second compartment 23, at least one accommodation recess 24, at least one opening 221, at least one outlet 231, at least one notch 211, at least one flow of gas F and at least one gas flowing in one way G. The slim-type portable device 5 further includes at least one casing 51 including at least one inlet 511. The number of the gas detecting module 100, the carrying plate 1, the compartment body 2, the actuator 3, the sensor 4, the substrate 11, the gas opening 12, the partition plate 21, the first compartment 22, the second compartment 23, the accommodation recess 24, the opening 221, the outlet 231, the notch 211, the flow of gas, the casing 51, the inlet 511 and the gas flowing in one way G is exemplified by one for each in the following embodiments but not limited thereto. It is noted that each of the gas detecting module 100, the carrying plate 1, the compartment body 2, the actuator 3, the sensor 4, the substrate 11, the gas opening 12, the partition plate 21, the first compartment 22, the second compartment 23, the accommodation recess 24, the opening 221, the outlet 231, the notch 211, the flow of gas, the casing 51, the inlet 511 and the gas flowing in one way G can also be provided in plural numbers.

A gas detecting module 100 is provided herein. Please refer to FIGS. 1A to 1C. In this embodiment, the gas detecting module 100 includes a carrying plate 1, a compartment body 2, an actuator 3 and a sensor 4. The carrying plate 1 includes a substrate 11 provided with a gas opening 12. The compartment body 2 includes a partition plate 21, and the interior of the compartment body 2 is divided into a first compartment 22 and a second compartment 23 by the partition plate 21. The first compartment 22 has an opening 221. In this embodiment, the opening 221 is located at the bottom of the first compartment 22, but not limited thereto. The second compartment 23 has an outlet 231. The outlet 231 is located at the bottom of the second compartment 23, but not limited thereto. The partition plate 21 has a notch 211 for allowing the first compartment 22 and the second compartment 23 to be in fluid communication with each other. The bottom of the compartment body 2 has an accommodation recess 24. The accommodation recess 24 allows the carrying plate 1 to be partially received and positioned therein, so that the bottom of the compartment body 2 is covered by the carrying plate 1, and the gas opening 12 of the substrate 11 is aligned with the outlet 231 of the second compartment 23.

In this embodiment, the sensor 4 is packaged on and electrically connected to the substrate 11 of the carrying plate 1. In such way, when the carrying plate 1 is assembled within the accommodation recess 24 of the compartment body 2, the sensor 4 penetrates the opening 221 of the first compartment 22 and is disposed within the first compartment 22 for measuring the gas within the first compartment 22.

In this embodiment, the actuator 3 is disposed within the second compartment 23. Since the actuator 3 in the second compartment 23 and the sensor 4 in the first compartment 22 are separated from each other by the partition plate 21, the heat generated from the actuator 3 is blocked by the partition plate 21 while the actuator 3 is actuated. In such way, the detection result of the sensor 4 is not adversely affected. Moreover, the actuator 3 covers the bottom of the second compartment 23 and is actuated to generate a flow of gas F that flows out of the outlet 231 of the second compartment 23, and then is discharged into an environment outside the compartment body 2 via the gas opening 12 of the substrate 11.

Figure 2:
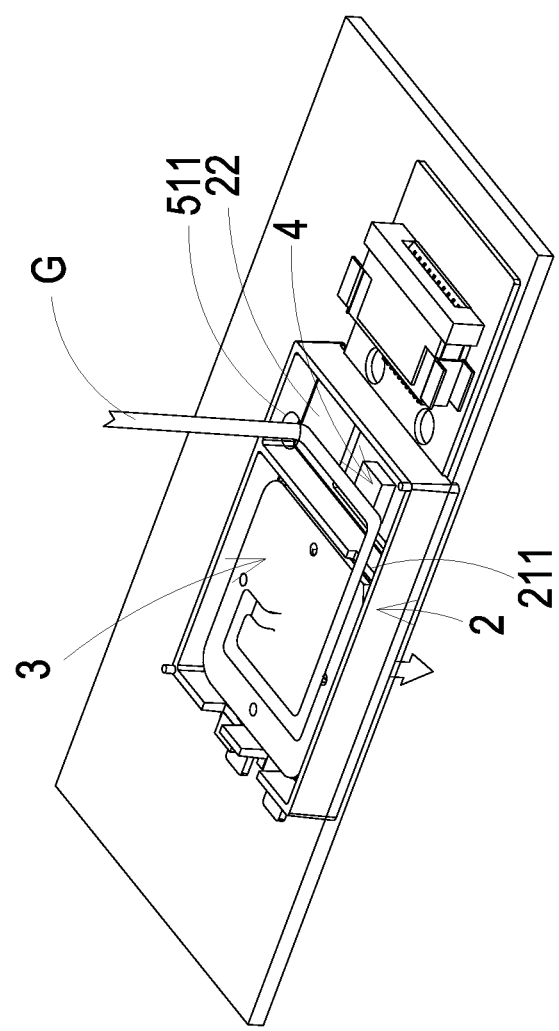
FIG. 2 is a schematic perspective view illustrating the gas guided direction of the gas detecting module applied in a slim-type portable device.
Figure 3A:
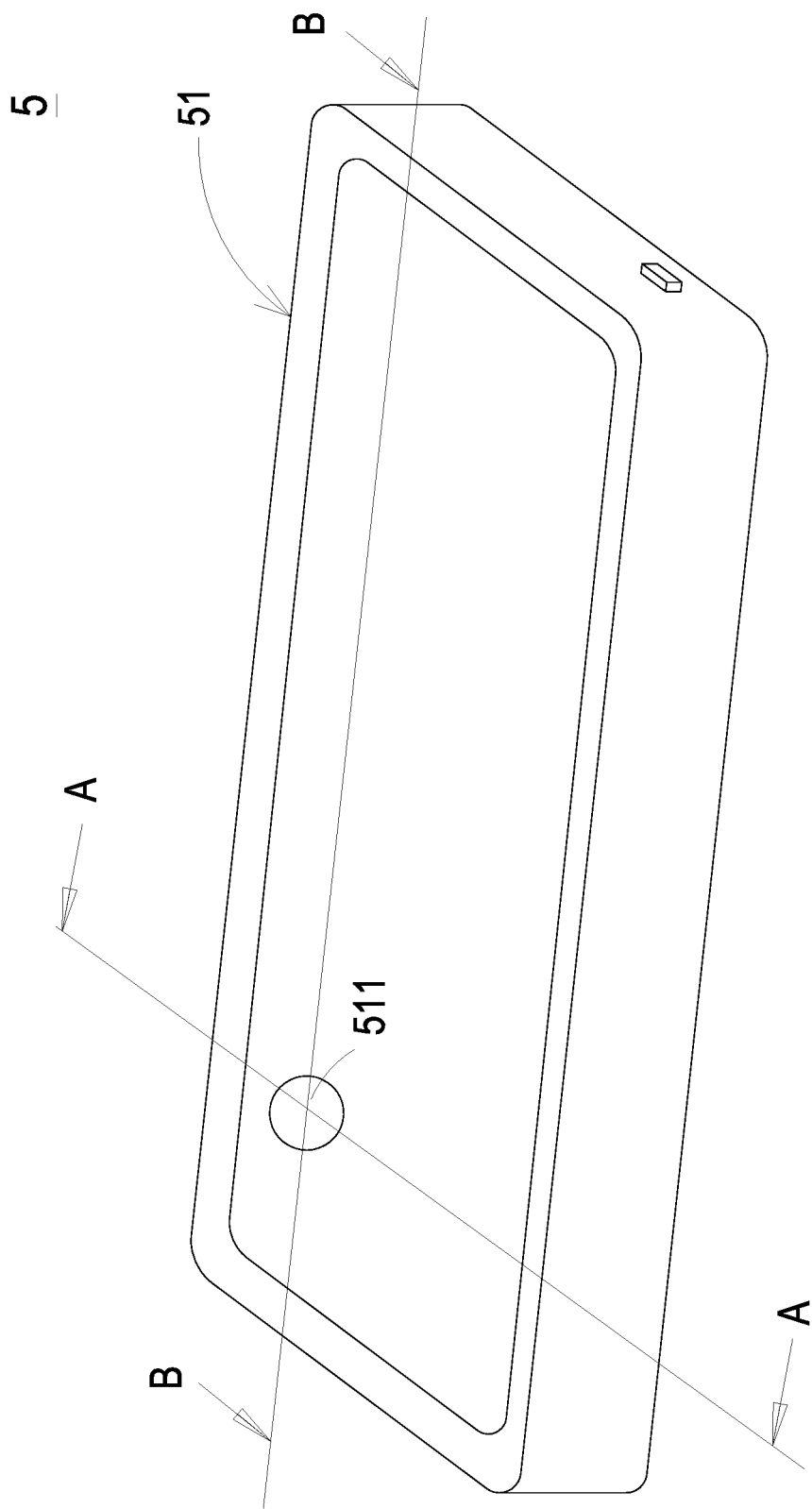
FIG. 3A is a schematic perspective view illustrating the inlet of the slim-type portable device of FIG. 2.
Figure 3B:
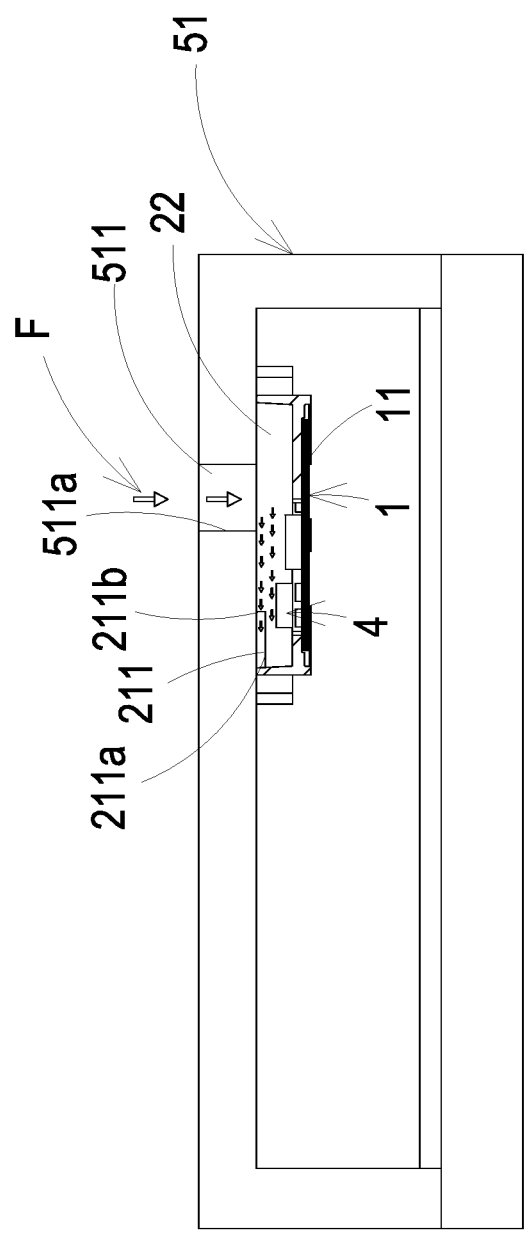
FIG. 3B is a schematic cross-sectional view illustrating the section of the slim-type portable device and the gas detecting module and taken along the line A-A of FIG. 3A.
Figure 3C:
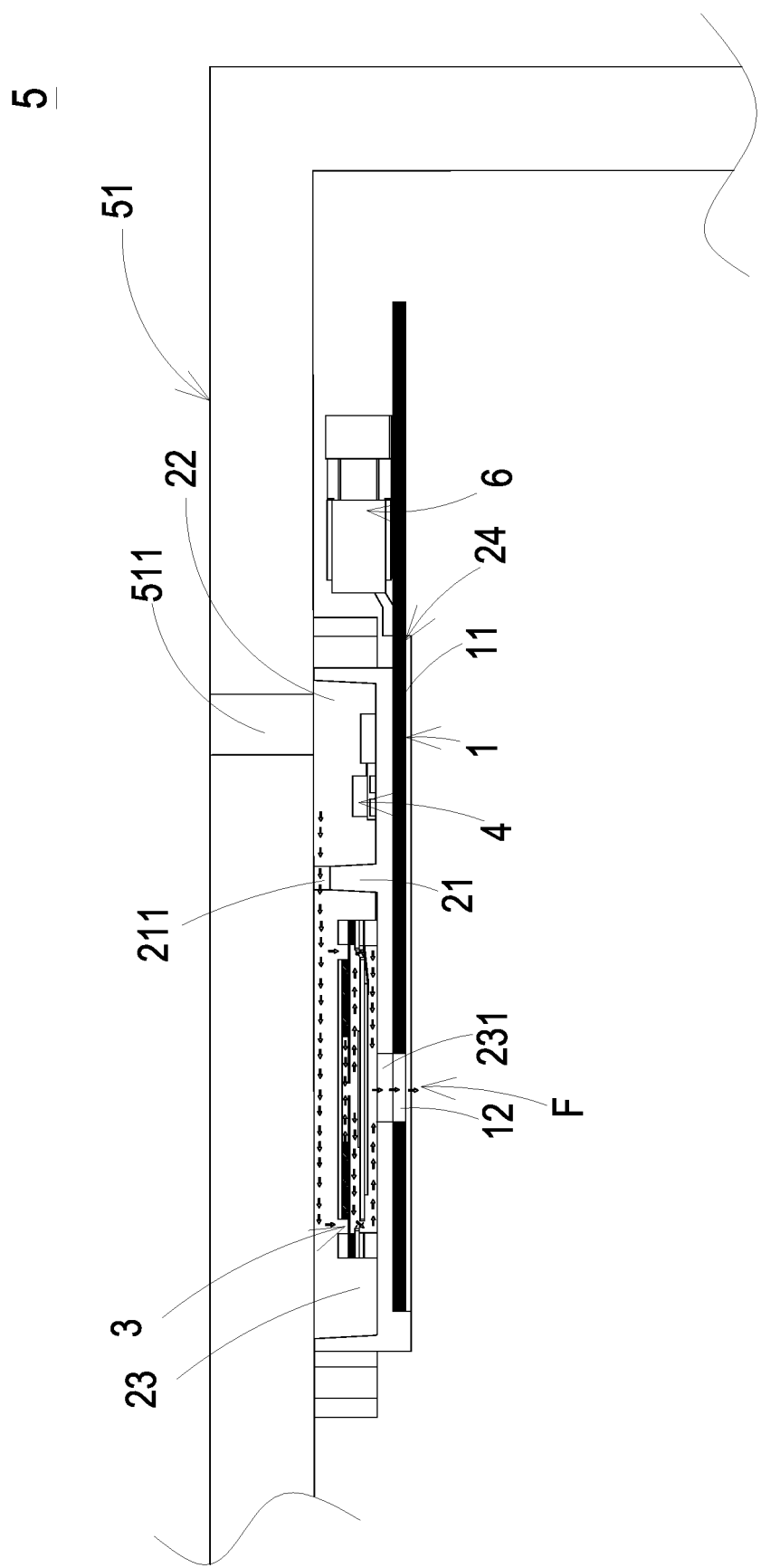
FIG. 3C is a schematic cross-sectional view illustrating the section of the slim-type portable device and the gas detecting module and taken along the line B-B of FIG. 3A.

Please refer to FIGS. 2 and 3A to 3C. FIG. 2 is a schematic perspective view illustrating the flow direction of the gas. FIG. 3A is a schematic perspective view illustrating the inlet of the slim-type portable device of FIG. 2. FIG. 3B is a schematic cross-sectional view taken along the line A-A of FIG. 3A. FIG. 3C is a schematic cross-sectional view taken along the line B-B of FIG. 3A. The gas detecting module 100 is assembled in a slim-type portable device 5. The slim-type portable device 5 includes a casing 51, and the casing 51 includes an inlet 511. When the gas detecting module 100 is assembled in the slim-type portable device 5, the inlet 511 of the casing 51 is aligned with the first compartment 22 of the compartment body 2, so that the first compartment 22 of the compartment body 2 is located under the inlet 511 of the casing 51. In other words, the slim-type portable device 5 has the casing 51 and the inlet 511 formed on the casing 51, and the casing 51 houses the gas detecting module 100 and the inlet 511 is aligned with the first compartment 22. In this embodiment, the inlet 511 of the casing 51 and the sensor 4 within the first compartment 22 are not aligned with each other. That is, the inlet 511 is not disposed directly above the sensor 4, and the inlet 511 and the sensor 4 are misaligned with each other.

Figure 1C:
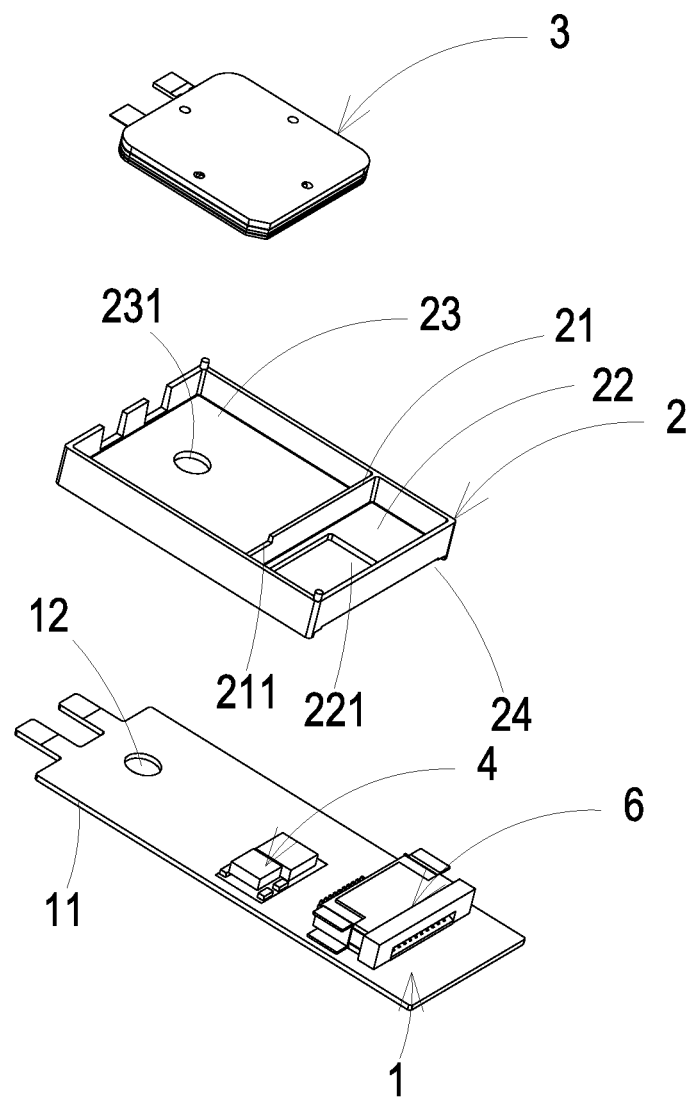
FIG. 1C is a schematic exploded view illustrating the gas detecting module of FIG. 1A.

Please refer to FIGS. 3B and 3C again. The notch 211 has a base surface 211a and a side surface 211b extending from the base surface 211a, as shown in FIG. 3B. The base surface 211a extends toward an inner wall 511a of the inlet 511, and connects to the side surface 211b at the position between two opposite edges of the opening 221 (as shown in FIG. 1C). The side surface 211b extends from the base surface 211a to the interior of the casing 51. In this way, the partition plate 21 has the notch 211 opened corresponding to the sensor 4. Both of the notch 211 and the sensor 4 are disposed on the same side of the first compartment 22 (i.e., the left side relative to the inlet 511 illustrated in FIG. 3B). When the actuator 3 is actuated, a negative pressure is formed in the second compartment 23, so that the ambient gas around the slim-type portable device 5 is inhaled into the first compartment 22 through the inlet 511. The sensor 4 within the first compartment 22 measures the gas flowing through the surface of the sensor 4 so as to monitor air quality around the slim-type portable device 5. As the actuator 3 is actuated continuously, the gas is transported to the second compartment 23 through the notch 211 of the partition plate 21, and then the gas is discharged into the environment outside the compartment body 2 via the outlet 231 and the gas opening 12 of the substrate 11. In such way, the gas flows in one way and is monitored (as illustrated by the arrows in FIG. 2, FIG. 3B and FIG. 3C). More specifically, the gas flows along one path from the inlet 511, the first compartment 22, the notch 211, the second compartment 23, the actuator 3, the outlet 231, the gas opening 12, to the environment outside the compartment body 2.

In this embodiment, the sensor 4 can be a gas sensor at least one selected from the group consisting of an oxygen sensor, a carbon monoxide sensor, a carbon dioxide sensor, a temperature sensor, an ozone sensor, a volatile organic compound sensor and combinations thereof. In some embodiments, the sensor 4 can be at least one selected from the group consisting of a bacterial sensor, a virus sensor, a microorganism sensor and combinations thereof.

The technical characteristics of the gas detecting module 100 are described as the above. The structures and actions of the actuator 3 are described as the following.

Figure 4A:
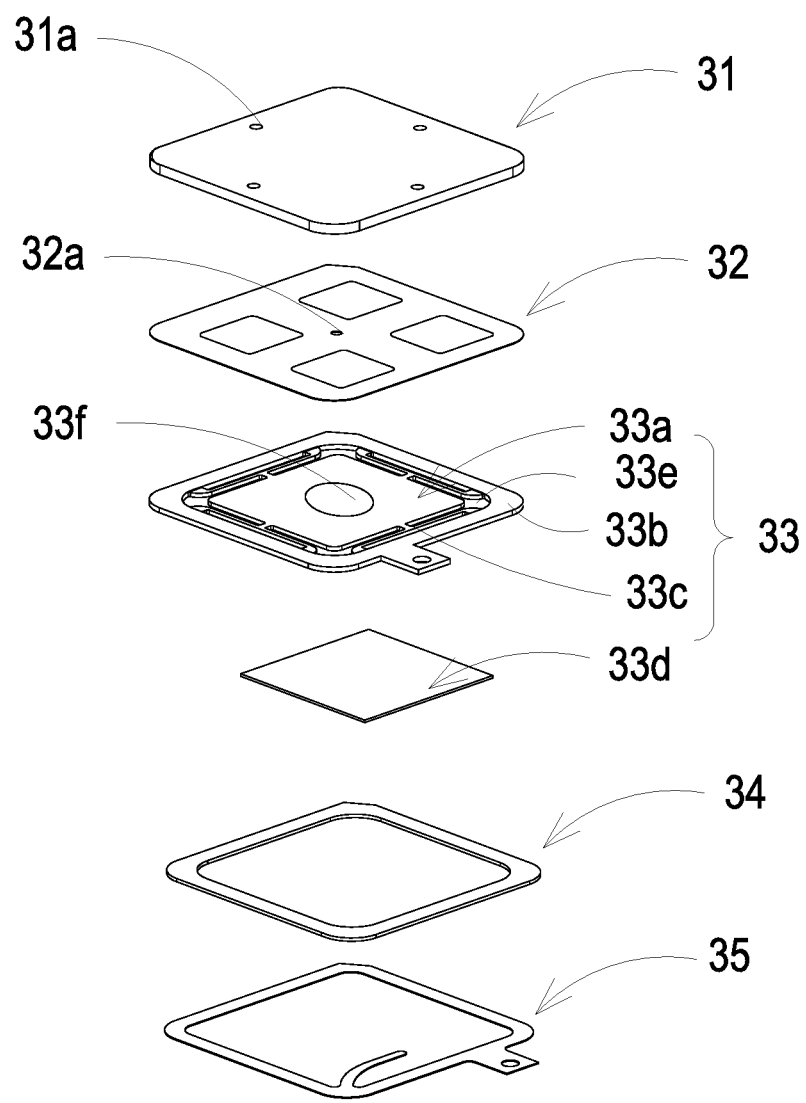
FIG. 4A is a schematic exploded view illustrating the actuator of the gas detecting module according to the embodiment of the present disclosure.
Figure 4B:
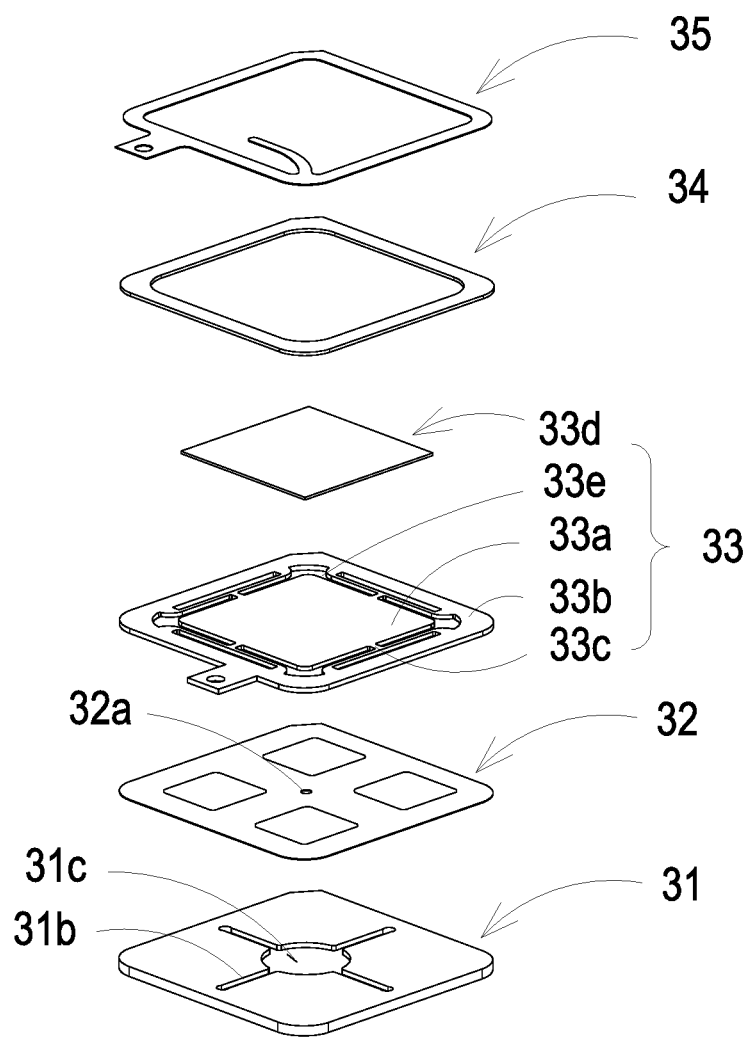
FIG. 4B is a schematic exploded view illustrating the actuator of FIG. 4A and taken along another viewpoint.
Figure 5A:
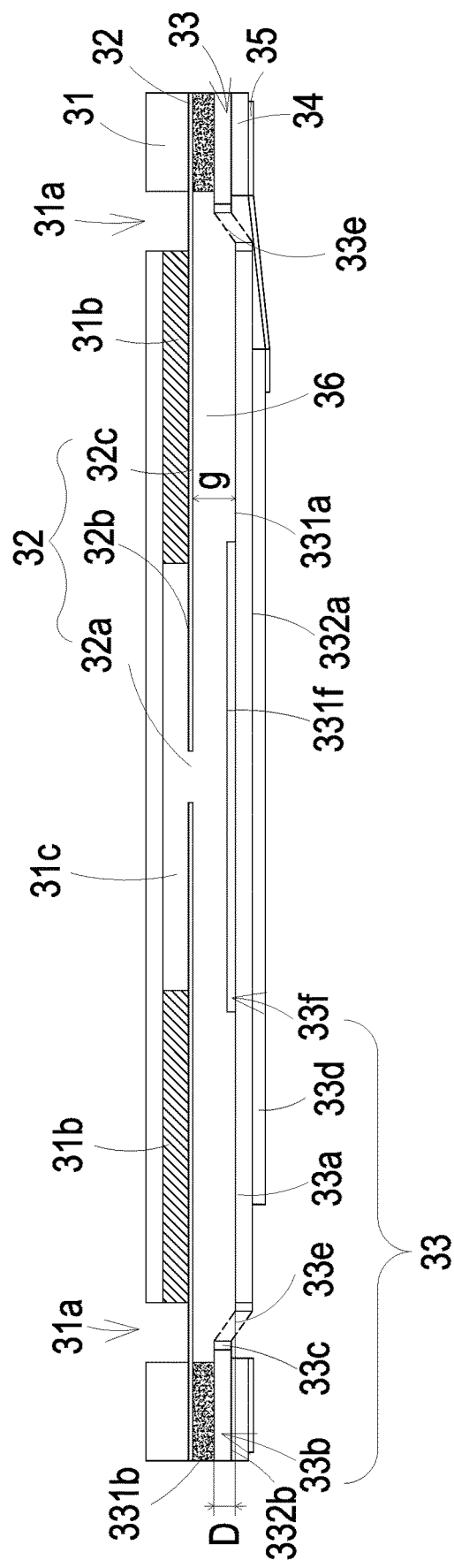
FIG. 5A is a schematic cross-sectional view illustrating the actuator of FIG. 4A.

Please refer to FIGS. 4A, 4B and 5A. In an embodiment, the actuator 3 is a gas pump. The actuator 3 includes a gas inlet plate 31, a resonance plate 32, a piezoelectric actuator 33, an insulation plate 34 and a conducting plate 35, which are stacked on each other sequentially. The gas inlet plate 31 has at least one inlet aperture 31a, at least one convergence channel 31b and a convergence chamber 31c. The number of the inlet aperture 31a is the same as the number of the convergence channel 31b. In this embodiment, the number of the inlet apertures 31a and the convergence channels 31b is exemplified by four for each but not limited thereto. The four inlet apertures 31a penetrate through the four convergence channels 31b respectively, and the four convergence channels 31b converge to the convergence chamber 31c.

The resonance plate 32 is assembled on the gas inlet plate 31 by attaching. The resonance plate 32 has a central aperture 32a, a movable part 32b and a fixed part 32c. The central aperture 32a is located in the center of the resonance plate 32 and is aligned with the convergence chamber 31c of the gas inlet plate 31. The region of the resonance plate 32 around the central aperture 32a and corresponding to the convergence chamber 31c is the movable part 32b. The region of the periphery of the resonance plate 32 securely attached on the gas inlet plate 31 is the fixed part 32c.

The piezoelectric actuator 33 includes a suspension plate 33a, an outer frame 33b, at least one connection component 33c, a piezoelectric element 33d, at least one vacant space 33e and a bulge 33f. The suspension plate 33a is a square suspension plate and has a first surface 331a and a second surface 332a. The first surface 331a and the second surface 332a are opposed to each other. The outer frame 33b is disposed around the periphery of the suspension plate 33a. The outer frame 33b has a coupling surface 331b and a bottom surface 332b opposite to the coupling surface 331b. The at least one connection component 33c is connected between the suspension plate 33a and the outer frame 33b for elastically supporting the suspension plate 33a. The at least one vacant space 33e is formed among the suspension plate 33a, the outer frame 33b and the at least one connection component 33c for allowing the gas to flow through.

In addition, the bulge 33f is formed on the first surface 331a of the suspension plate 33a. In this embodiment, the formation of the bulge 33f may be completed by using an etching process, in which the region between the periphery of the bulge 33f and the junction at the connection component 33c is partially removed. Accordingly, the bulge 33f of the suspension plate 33a is higher than the first surface 331a, and a stepped structure is formed.

As shown in FIG. 5A, in this embodiment, the suspension plate 33a may be processed by a stamping method, by which the outer frame 33b, the connection component 33c, and the suspension plate 33a have a concave profile in cross section. The stamping method makes the suspension plate 33a disposed further away from the resonance plate 32a distance D, which can be adjusted by the at least one connection component 33c formed between the suspension plate 33a and the outer frame 33b. Consequently, the top surface 331f of the bulge 33f and the first surface 331a of the suspension plate 33a are not coplanar with the coupling surface 331b of the outer frame 33b. Namely, the top surface 331f of the bulge 33f and the first surface 331a are lower than the coupling surface 331b of the outer frame 33b, and the second surface 332a of the suspension plate 33a is lower than the bottom surface 332b of the outer frame 33b. In the embodiment, the piezoelectric element 33d is attached on the second surface 332a of the suspension plate 33a and aligned with the bulge 33f. In response to an applied voltage, the piezoelectric element 33d is deformed by the piezoelectric effect to drive the suspension plate 33a to undergo the bending vibration. By utilizing a small amount of adhesive applied to the coupling surface 331b of the outer frame 33b, the piezoelectric actuator 33 is attached to the fixed part 32c of the resonance plate 32 after a heat pressing process, thereby assembling the piezoelectric actuator 33 and the resonance plate 32 in combination.

In addition, the insulation plate 34 and the conducting plate 35 are both thin frame-shaped sheets, which are sequentially stacked under the piezoelectric actuator 33. In the embodiment, the insulation plate 34 is attached to the bottom surface 332b of the outer frame 33b of the piezoelectric actuator 33.

Please refer to FIG. 5A again. After the gas inlet plate 31, the resonance plate 32, the piezoelectric actuator 33, the insulation plate 34 and the conducting plate 35 of the actuator 3 are stacked and assembled sequentially, a chamber gap g is formed between the first surface 331a of the suspension plate 33a and the resonance plate 32. Since the distance between the suspension plate 33a and the resonance plate 32 will influence the transportation effect of the actuator 3, it is very important to maintain the chamber gap g for providing a stable transportation efficiency of the actuator 3. The suspension plate 33a of the actuator 3 is processed by the stamping method as described above, and it makes the suspension plate 33a disposed further away from the resonance plate 32. Consequently, the first surface 331a of the suspension plate 33a and the coupling surface 331b of the outer frame 33b are non-coplanar. Namely, the top surface 331f of the bulge 33f and the first surface 331a of the suspension plate 33a are lower than the coupling surface 331b of the outer frame 33b, and the second surface 332a of the suspension plate 33a is lower than the bottom surface 332b of the outer frame 33b. In this way, the entire structure may be improved by adopting the stamping method to process the suspension plate 313a. The space between the suspension plate 33a of the piezoelectric actuator 33 and the resonance plate 32 is adjustable due to the stamping method, by which the adjustable chamber gap g is realized. That is, the design of a chamber space 36 is improved by processing the suspension plate 33a of the piezoelectric actuator 33 to be disposed further away from the resonance plate 22. The desired chamber gap g can be satisfied by simply adjusting the distance D, as described above. It simplifies the structural design regarding the adjustment of the chamber gap g, and it also achieves the advantages of simplifying the process and shortening the processing time.

Figure 5B:
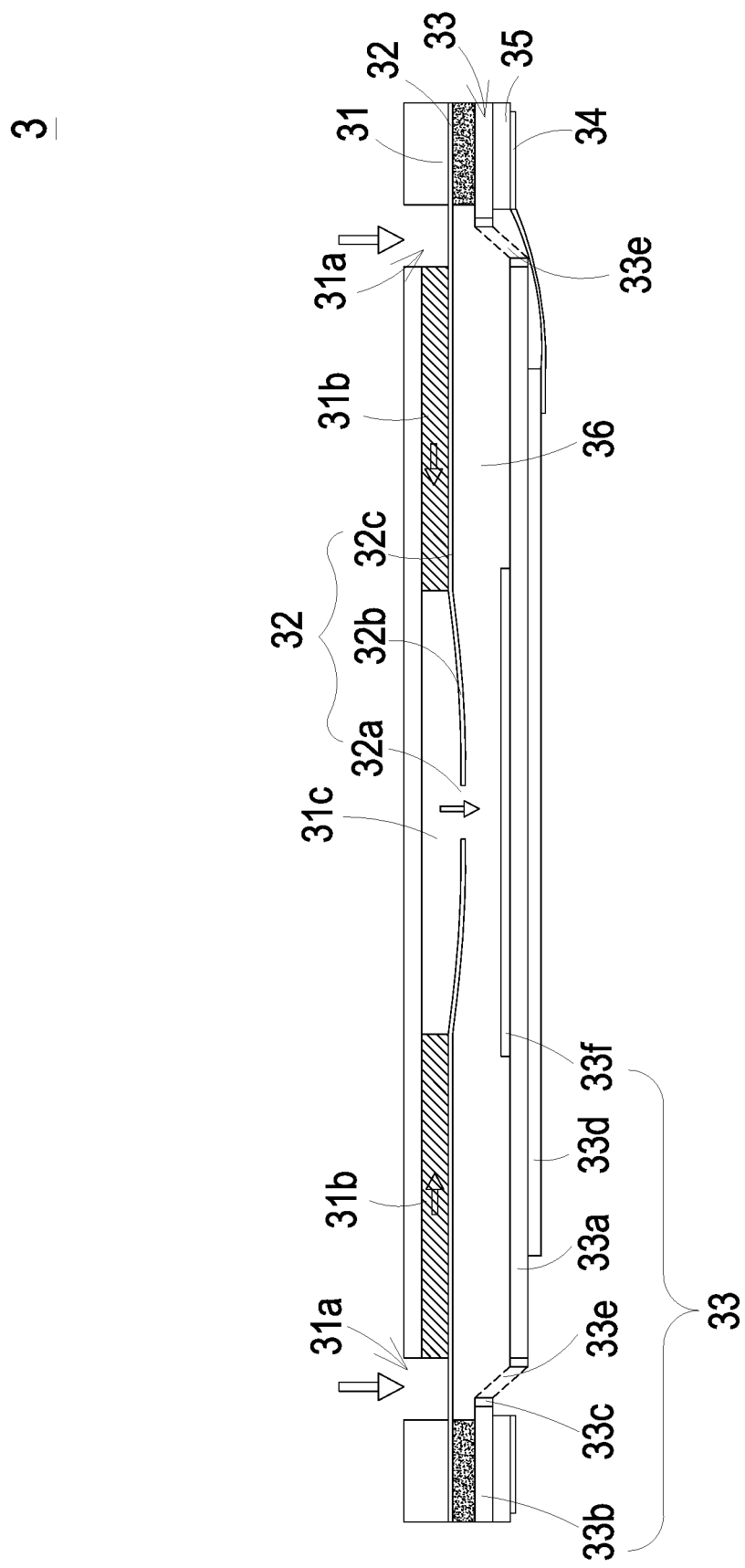
FIGS. 5B, 5C and 5D schematically illustrate the actions of the actuator of FIG. 5A.
Figure 5C:
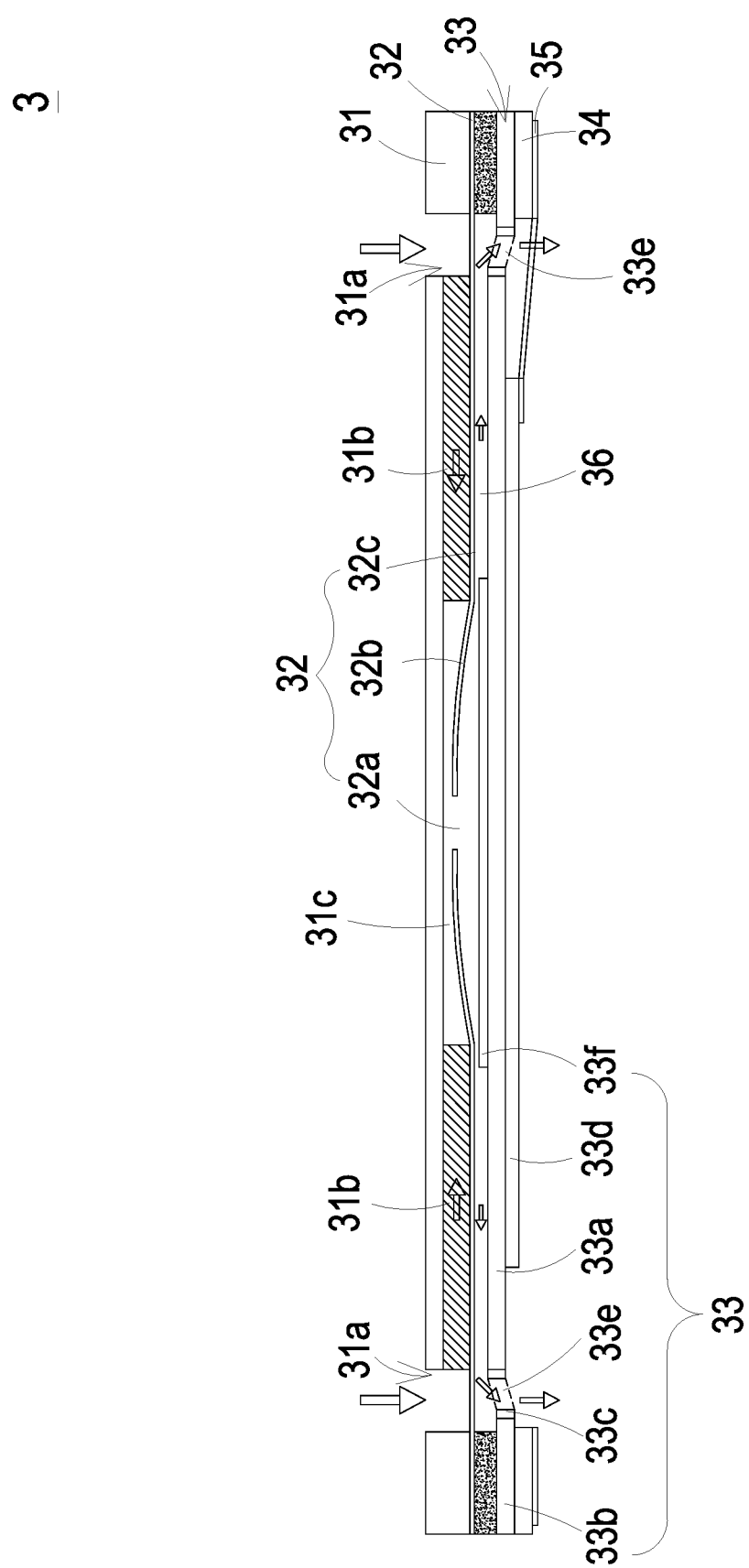
Figure 5D:
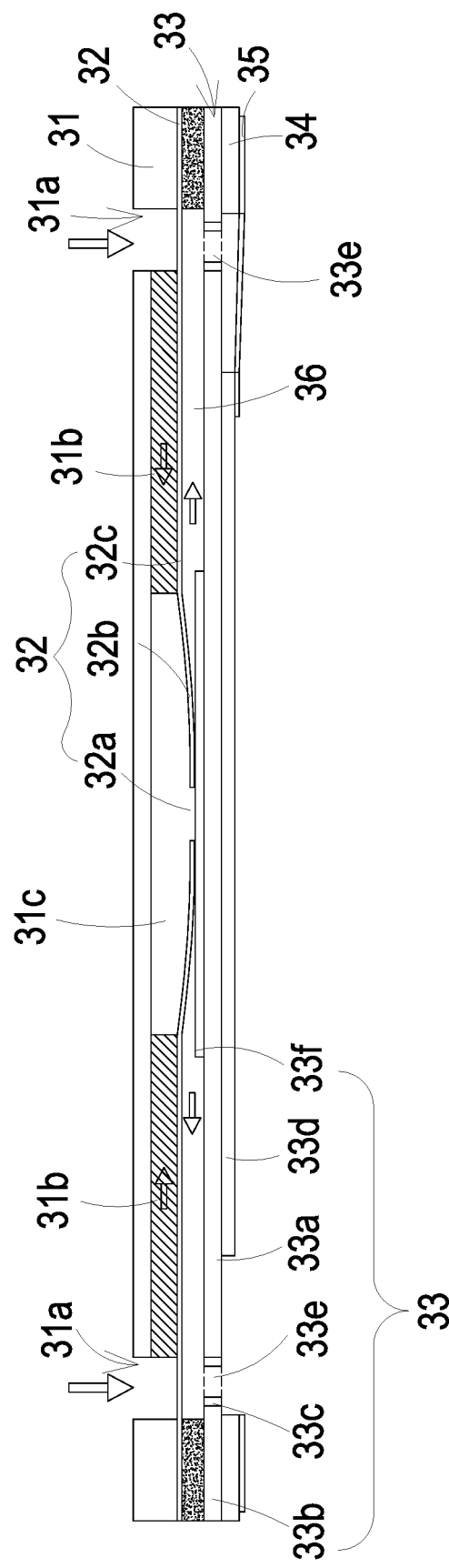

FIGS. 5B and 5D are schematic views illustrating actions of the actuator of FIG. 5A. Please refer to FIG. 5B firstly. When the piezoelectric element 33d of the piezoelectric actuator 33 is deformed in response to an applied voltage, the suspension plate 33a is driven to displace in the direction away from the gas inlet plate 31. In that, the volume of the chamber space 36 is increased, a negative pressure is formed in the chamber space 36, and the gas in the convergence chamber 31c is inhaled into the chamber space 36. At the same time, the resonance plate 32 is in resonance and thus displaced synchronously in the direction away from the gas inlet plate 31. Thereby, the volume of the convergence chamber 31c is increased. Since the gas in the convergence chamber 31c flows into the chamber space 36, the convergence chamber 31c is also in a negative pressure state, and the gas is sucked into the convergence chamber 31c by flowing through the inlet aperture 31a and the convergence channel 31b. Please refer to FIG. 5C, the piezoelectric element 33d drives the suspension plate 33a to be displaced toward the gas inlet plate 31 to compress the chamber space 36. Thus, the gas contained in the chamber space 36 is transported to flow through the vacant spaces 33e in the direction away from the gas inlet plate 31 and it achieves the effect of gas transportation. Similarly, the resonance plate 32 is actuated in resonance by the suspension plate 33a and displaced toward the gas inlet plate 31. Thus, the gas contained in convergence chamber 31c is compressed synchronously to flow to the chamber space 36. Finally, as shown in FIG. 5D. When the suspension plate 33a is driven to displace in the direction away from the gas inlet plate 31, the resonance plate 32 is also driven to displace in the direction away from the gas inlet plate 31 at the same time. In that, the resonance plate 32 pushes the gas in the chamber space 36 toward the vacant space 33e, and the volume of the convergence chamber 31c is increased. Thus, the gas can continuously flow through the inlet aperture 31a and the convergence channel 31b and be converged in the convergence chamber 31c. By repeating the actions shown in the above continuously, the actuator 3 can continuously inhale the gas through the inlet aperture 31a and transport the gas through the vacant spaces 33e in the direction away from the gas inlet plate 31. It achieves the effect of transporting the gas outside the gas detecting module 100 to the sensor 4 for detecting, thereby improving the detecting efficiency.

Please refer to FIG. 5A again. In another embodiment, the actuator 3 can be a micro-electromechanical system gas pump formed by a micro-electromechanical system method. The gas inlet plate 31, the resonance plate 32, the piezoelectric actuator 33, the insulation plate 34, and the conducting plate 35 can all be made through a surface micromachining technique to reduce the volume of the actuator 3.

Please refer to FIG. 1 again. In an embodiment, the substrate 11 may be a circuit board and includes a connector 6 disposed thereon for allowing a flexible circuit board (not shown) to be inserted thereinto. Consequently, the substrate 11 is provided with electrical connection and signal communication.

From the above descriptions, the gas detecting module is capable of monitoring the air quality in the environment in any time. With the design of the concave profile, the actuator can inhale the gas into the interior of the gas detecting module rapidly and stably, so that the sensing efficacy of the sensor is enhanced. Since the sensor in the first compartment and the actuator in the second compartment are separated from each other by the partition plate, interfering factors generated from the actuator is blocked by the partition plate. In addition, when the gas detecting module is assembled and applied in the slim-type portable device for detecting gas, the detection result of the sensor is not adversely affected by the processor or other components within the slim-type portable device. In other words, the gas detecting module can be applied in the slim-type portable device and monitor the air quality in the environment rapidly and accurately at anytime and anywhere.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A slim-type portable device, comprising: a gas detecting module comprising: a carrying plate having a substrate provided with a gas opening; a sensor packaged on and electrically connected to the substrate; a compartment body having a partition plate disposed therein to divide an interior of the compartment body into a first compartment and a second compartment, wherein the first compartment has an opening, the second compartment has an outlet, and the bottom of the compartment body has an accommodation recess for allowing the carrying plate to be partially received and positioned therein, so that the bottom of the compartment body is covered by the carrying plate and the gas opening of the substrate is aligned with the outlet of the second compartment, wherein the sensor disposed on the substrate penetrates the opening and is disposed within the first compartment, and the partition plate has a notch for allowing the first compartment and the second compartment to be in fluid communication with each other; and an actuator disposed within the second compartment and separated from the sensor disposed within the first compartment so that the heat generated from the actuator is blocked from affecting the detection result of the sensor, wherein the actuator covers the bottom of the second compartment and is actuated to generate a flow of gas that flows out of the outlet of the second compartment, and then is discharged into an environment outside the compartment body via the gas opening of the substrate; and wherein the slim-type portable device further comprises: a casing having an inlet, wherein the casing houses the gas detecting module, and the inlet is aligned with the first compartment of the compartment body, whereby as the actuator is actuated, the gas around the slim-type portable device is inhaled into the first compartment through the inlet, and the sensor measures the gas flowing through the surface of the sensor, and then the gas is transported to the second compartment through the notch of the partition plate and is discharged into the environment outside the compartment body via the outlet and the gas opening of the substrate, so that the gas flows in one way and is monitored.

2. The slim-type portable device according to claim 1, wherein the inlet of the casing is misaligned with the sensor disposed in the first compartment.

3. The slim-type portable device according to claim 1, wherein the sensor is a gas sensor.

4. The slim-type portable device according to claim 3, wherein the gas sensor is at least one selected from a group consisting of an oxygen sensor, a carbon monoxide sensor, a carbon dioxide sensor, and combinations thereof.

5. The slim-type portable device according to claim 3, wherein the gas sensor is a volatile organic compound sensor.

6. The slim-type portable device according to claim 3, wherein the sensor is at least one selected from a group consisting of a bacterial sensor, a virus sensor, a microorganism sensor, and combinations thereof.

7. The slim-type portable device according to claim 1, wherein the actuator is a micro-electromechanical system gas pump.

8. The slim-type portable device according to claim 1, wherein the actuator is a gas pump, and the gas pump comprises:

a gas inlet plate having at least one inlet aperture, at least one convergence channel and a convergence chamber, wherein the at least one inlet aperture allows the gas to flow in, and the at least one convergence channel is aligned with the at least one inlet aperture and guides the gas from the inlet aperture toward the convergence chamber;
a resonance plate having a central aperture and a movable part, wherein the central aperture is aligned with the convergence chamber, and the movable part surrounds the central aperture; and
a piezoelectric actuator aligned with the resonance plate;
wherein a chamber space is formed between the resonance plate and the piezoelectric actuator, so that the gas from the at least one inlet aperture of the gas inlet plate is converged to the convergence chamber along the at least one convergence channel and flows into the chamber space through the central aperture of the resonance plate when the piezoelectric actuator is driven, whereby the gas is further transported through a resonance between the piezoelectric actuator and the movable part of the resonance plate.

9. The slim-type portable device according to claim 8, wherein the piezoelectric actuator comprises:
a suspension plate having a first surface and a second surface opposite to the first surface;
an outer frame arranged around the suspension plate and having a coupling surface;
at least one connection component connected between the suspension plate and the outer frame for elastically supporting the suspension plate; and
a piezoelectric element attached on the second surface of the suspension plate to drive the suspension plate to undergo a bending vibration in response to an applied voltage;
wherein the at least one connection component is formed between the suspension plate and the outer frame, the first surface of the suspension plate and the coupling surface of the outer frame are non-coplanar, and a chamber gap is maintained between the first surface of the suspension plate and the resonance plate.

10. The slim-type portable device according to claim 9, wherein the suspension plate is square and has a bulge formed on the first surface thereof.

11. The slim-type portable device according to claim 8, wherein the gas pump comprises a conducting plate and an insulation plate, and the gas inlet plate, the resonance plate, the piezoelectric actuator, the insulation plate and the conducting plate are stacked sequentially.

12. The slim-type portable device according to claim 1, wherein the substrate is a circuit board and includes a connector disposed thereon for allowing a flexible circuit board to be inserted thereinto, whereby the substrate is provided with electrical connection and signal communication.

13. A slim-type portable device, comprising: at least one gas detecting module comprising: at least one carrying plate having at least one substrate provided with at least one gas opening; at least one sensor packaged on and electrically connected to the substrate; at least one compartment body having at least one partition plate disposed therein to divide an interior of the compartment body into at least one first compartment and at least one second compartment, wherein the first compartment has at least one opening, the second compartment has at least one outlet, and the bottom of the compartment body has at least one accommodation recess for allowing the carrying plate to be partially received and positioned therein, so that the bottom of the compartment body is covered by the carrying plate, and the gas opening of the substrate is aligned with the outlet of the second compartment, wherein the sensor disposed on the substrate penetrates the opening and is disposed within the first compartment, and the partition plate has at least one notch for allowing the first compartment and the second compartment to be in fluid communication with each other; and at least one actuator disposed within the second compartment and separated from the sensor disposed within the first compartment so that the heat generated from the actuator is blocked from affecting the detection result of the sensor, wherein the actuator covers the bottom of the second compartment and is actuated to generate a flow of gas that flows the outlet of the second compartment, and then is discharged into an environment outside the compartment body via the gas opening of the substrate; and wherein the slim-type portable device further comprises: at least one casing having at least one inlet, wherein the casing houses the gas detecting module, and the inlet is aligned with the first compartment of the compartment body, whereby as the actuator is actuated, the gas around the slim-type portable device is inhaled into the first compartment through the inlet, and the sensor measures the gas flowing through the surface of the sensor, and then the gas is transported to the second compartment through the notch of the partition plate and is discharged into the environment outside the compartment body via the outlet and the gas opening of the substrate, so that the gas flows in one way and is monitored.

* * * * *